(12) United States Patent
Huang et al.

(10) Patent No.: US 6,713,280 B1
(45) Date of Patent: Mar. 30, 2004

(54) ENHANCEMENT OF PEPTIDE CELLULAR UPTAKE

(75) Inventors: Ziwei Huang, Philadelphia, PA (US); Jialun Wang, Cherry Hill, NJ (US); Zhijia Zhang, Cherry Hill, NJ (US); Simei Shan, Voorhees, NJ (US); Zhixian Lu, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/544,664

(22) Filed: Apr. 6, 2000

Related U.S. Application Data

(60) Provisional application No. 60/128,202, filed on Apr. 7, 1999.

(51) Int. Cl.⁷ .................................................. C12P 21/06
(52) U.S. Cl. ...................... 435/69.1; 530/300; 530/350; 514/8
(58) Field of Search .................... 435/69.1; 530/300, 530/350; 514/8

(56) References Cited

U.S. PATENT DOCUMENTS

| 5,108,921 A | 4/1992 | Low et al. ................ 435/240.1 |
| 5,550,111 A | 8/1996 | Suhadolnik et al. ........... 514/44 |
| 5,856,445 A | * 1/1999 | Korsmeyer .................. 530/350 |

FOREIGN PATENT DOCUMENTS

| WO | WO 90/10448 | 9/1990 |
| WO | WO 91/04753 | 4/1991 |

OTHER PUBLICATIONS

Hongbin Zha and John C. Reed, "Heterodimerization–Independent Functions of Cell Death Regulatory Proteins BAX and Bcl–2 in Yeast and Mammalian Cells", *The Journal of Biological Chemistry*, vol. 272, No. 50, pp. 31482–31–488 (Dec. 12, 1997).
Sedlak et al., "Multiple Bcl–2 Family Members Demonstrate Selective Dimerizations with BAX", *Proc. Natl. Acad. Sci. USA—Cell Biology*, vol. 92, pp. 7834–7834 (Aug. 1995).
Yin et al.,"BH1 and BH2 Domains of Bcl–2 are Required for Inhibition of Apoptosis and Heterodimerization with BAX", *Nature*, vol. 369 pp. 31482–31488 (May 26, 1994).
Sattler et al., "Structure of Bcl–$x_L$–Bak Peptide Complex: Recognition Between Regulators of Apoptosis", *Science*, vol. 275 pp. 983–986(Feb. 14, 1997).
Kekekar et al., "BAD is a BH3 Domain–Containing Protein That Forms an Inactivating Dimer with Bcl–$x_L$", *Molecular and Cellular Biology*, vol. 17, No. 12, pp. 7040–7046 (Dec. 1997).
Sato et al., "Interactions Among Members of the Bcl–2 Protein Family Analyzed with a Yeast Two–Hybrid System", *Proc. Natl. Acad. Sci. USA—Cell Biology*, vol. 91, pp. 9238–9242 (Sep. 1994).

Craig B. Thompson, "Apoptosis in the Pathogenesis and Treatment of Disease", *Science*, vol. 267 pp. 1456–1462 (Mar. 10, 1995).
Chittenden et al., "A Conserved Domain in Bak, Distinct From BH1 and BH2, Mediates Cell Death and Protein Binding Functions", *EMBO J*, 14(22):5589–96 (Nov. 15, 1995).
Boyd et al., "Bik, A Novel Death–Inducing Protein Shares a Distinct Sequence Motif with Bcl–2 Family Proteins and Interacts with Viral and Cellular Survival–Promoting Proteins", *Oncogene*, 11(9):1921–8 (Nov. 2, 1995).
J.C. Reed, "Bcl–2 and the Regulation of Programmed Cell Death", *J Cell Biol.*, 124(1–2):1–6 (Jan. 1994).
E. Yang and S.J. Korsmeyer, "Molecular Thanatopsis: A Disclosure on the BCL2 Family and Cell Death", *Blood*, 88(2):386–401 (Jul. 15, 1996).
S.W. Muchmore, et al., "X–Ray and NMR Structure of Human Bcl–xL, an Inhibitor of Programmed Cell Death", *Nature*, 381(6580)335–41 (May 23, 1996).
Yoo, et al., "Apoptosis in Human Leukemic Cells Induced by lactoferricin, a Bovine Milk Protein–Derived Peptide: Involvement of Reactive Oxygen Species," *Biochemical and Biophysical Research Communications*, vol. 237, No. 3, 1997, pp. 624–628.
Resnicoff, et al., "A Novel Class of Peptides That Induce Apoptosis and Abrogate Tumorigenesis in Vivo," *Biochemical and Biophysical Research Communications*, vol. 240, No. 1, 1997, pp. 208–212.

(List continued on next page.)

*Primary Examiner*—Christopher R. Tate
*Assistant Examiner*—Maury Audet
(74) *Attorney, Agent, or Firm*—Drinker Biddle & Reath LLP

(57) ABSTRACT

Peptide conjugates of the formula are provided $$(R-X)_n\text{-peptide} \qquad (I)$$

wherein:
  n is from 1 to 10;
  X is
    (a) C=O, when the R—X group is attached to:
      (i) the N-terminus of the peptide, or
      (ii) a side chain of the peptide where the functional group of the side chain to which the R—X group is attached is $NH_2$ or OH; or
    (b) O or NH, when the R—X group is attached to
      (i) the C-terminus of the peptide, or
      (ii) a side chain of the peptide where the functional group of the side chain to which the R—X group is attached is COOH or $CONH_2$; and
  R is selected from the group consisting of $C_{2-18}$ alkyl; $C_{2-18}$ alkoxy; $C_{2-14}$ alkylenyl containing one or two double bonds; cyclobutyl; cyclopentyl; cyclohexyl optionally monosubstituted with a $C_{1-5}$ straight or branched chain alkyl group; phenyl optionally monosubstituted with a $C_{1-5}$ straight or branched chain alkyl group; and benzyl.

11 Claims, 6 Drawing Sheets

OTHER PUBLICATIONS

Welsh, et al., "Role of Apoptosis in the Regulation of Virus–Induced T Cell Responses, Immune Suppression, and Memory," *Journal of Cellular Biochemistry*, vol. 59, 1995, pp. 135–142.

Lee, et al., "Involvment of oxidation of LDL–induced collagen gene regulation in mesangial cells," *Kidney International*, vol. 50, 1996, pp. 1582–1590.

Zhu, et al., "Preparation of Vitamin $B_6$–Peptide–Oligonucleotide Conjugates," *Bioconjugate Chem*, vol. 5, No. 4, 1994, pp. 312–315.

Toth, et al., "Oral absorption of lipidic amino acid conjugates," *International Journal of Pharmaceutics*, vol. 102, 1994, pp. 223–230.

Swaan, et al., "Enhanced Transepithelial Transport of Peptides by Conjugation to Cholic Acid," *Bioconjugate Chem.*, vol. 8, No. 4, 1997, pp. 520–525.

Hussain, et al., "Synthesis and Structure Elucidation of γ–Aminobutyric Acid Conjugates with Lipidic Acids, Lipidic Amino Acids and Lipidic Peptides," *Liebigs Ann. Chem.*, 1991, pp. 963–966.

Gastman, et al., "Caspase–mediated Degradation of T–Cell Receptor ζ–Chain," *Cancer Research*, vol. 59,, Apr. 1, 1999, pp. 1422–1427.

Klehntopf, et al., "Cell–Permeable Peptides Covering the NIP–Recognition Site of BCL–2 and BCL–2 Specific Hammerhead Ribozymes Restore Sensisitivy of Multiple Myeloma Cells to Glucocorticoid–Induced Apoptosis," *Exp. Hematology*, vol. 23, No. 8, 1995, p. 905, Abstract #573.

Klehntopf, et al., "Resistance of Multiple Myeloma Cells to Glucocorticoid–Induced Apoptosis is Restored by Cell–Permeable Peptides targeting Functional Domains of BCL–2," *Onkologic*, vol. 18, Suppl. 2, 1995, p. 65, Abstract #195.

Liu, et al., "Thymic Peptides Induce Apoptosis in Undifferentiated Cancer Cells," *FASEB*, vol. 8, No. 4–5, 1994, pp. A773, Abstract #4482.

MPSEARCH, Oxford Molecular LTD., 1993–1998 for SEQ ID No. 1–26, SEQ ID No. 38–33 and SEQ ID No. 35–54.

* cited by examiner

SEQUENCE LISTING

<160> NUMBER OF SEQ ID NOS: 58

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 1

Asn Leu Trp Ala Ala Gln Arg Tyr Gly Arg Glu Leu Arg Arg Met Ser
 1               5                  10                  15

Asp Glu Phe Glu Gly Ser Phe Lys Gly Leu
            20                  25

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 2

Asn Leu Trp Ala Ala Gln Glu Tyr Gly Arg Glu Leu Arg Arg Met Ser
 1               5                  10                  15

Asp Glu Phe Val Asp Ser Phe Lys Lys Gly Leu
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 3

Asn Leu Trp Ala Ala Gln Arg Tyr Gly Arg Glu Leu Arg Arg Met Ser
 1               5                  10                  15

Asp Glu Phe Glu Gly Ser Phe Lys Gly Leu Pro
            20                  25

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 4

Pro Ser Ser Thr Met Gly Gln Val Gly Arg Gln Leu Ala Ile Ile Gly
 1               5                  10                  15

Asp Asp Ile Asn Arg Arg Tyr Asp Ser Glu Phe
            20                  25

<210> SEQ ID NO 5
<211> LENGTH: 27

```
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 5

Pro Asn Ser Ile Leu Gly Gln Val Gly Arg Gln Leu Ala Leu Ile Gly
 1               5                  10                  15

Asp Asp Ile Asn Arg Arg Tyr Asp Thr Glu Phe
            20                  25

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 6

Gln Asp Ala Ser Thr Lys Lys Leu Ser Glu Cys Leu Lys Arg Ile Gly
 1               5                  10                  15

Asp Glu Leu Asp Ser Asn Met Glu Leu Gln Arg
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 7

Gln Asp Ala Ser Thr Lys Lys Leu Ser Glu Cys Leu Arg Arg Ile Gly
 1               5                  10                  15

Asp Glu Leu Asp Ser Asn Met Glu Leu Gln Arg
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 8

Leu Arg Pro Ala Pro Pro Gly Val His Leu Ala Leu Arg Gln Ala Gly
 1               5                  10                  15

Asp Glu Phe Ser Arg Arg Tyr Gln Arg Asp Phe
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide
```

```
<400> SEQUENCE: 9

Leu Ser Pro Val Pro Pro Val Val His Leu Thr Leu Arg Gln Ala Gly
 1               5                  10                  15

Asp Asp Phe Ser Arg Arg Tyr Arg Arg Asp Phe
            20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 10

Leu Ser Pro Val Pro Pro Cys Val His Leu Thr Leu Arg Arg Ala Gly
 1               5                  10                  15

Asp Asp Phe Ser Arg Arg Tyr Arg Arg Asp Phe
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 11

Leu Ser Pro Val Pro Pro Val Val His Leu Thr Leu Arg Arg Ala Gly
 1               5                  10                  15

Asp Asp Phe Ser Arg Arg Tyr Arg Arg Asp Phe
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 12

Glu Ile Val Arg Ala Ser Asp Val Arg Gln Ala Leu Arg Asp Ala Gly
 1               5                  10                  15

Asp Glu Phe Glu Leu Arg Tyr Arg Arg Ala Phe
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 13

Glu Val Ile Pro Met Ala Ala Val Lys Gln Ala Leu Arg Glu Ala Gly
 1               5                  10                  15

Asp Glu Phe Glu Leu Arg Tyr Arg Arg Ala Phe
            20                  25
```

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 14

Gln Glu Asp Ile Ile Arg Asn Ile Ala Arg His Leu Ala Gln Val Gly
 1               5                  10                  15

Asp Ser Met Asp Arg Ser Ile Pro Pro Gly Leu
            20                  25

<210> SEQ ID NO 15
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 15

Gln Glu Glu Ile Ile His Asn Ile Ala Arg His Leu Ala Gln Ile Gly
 1               5                  10                  15

Asp Glu Met Asp His Asn Ile Gln Pro Thr Leu
            20                  25

<210> SEQ ID NO 16
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 16

Cys Met Glu Gly Ser Asp Ala Leu Ala Leu Arg Leu Ala Cys Ile Gly
 1               5                  10                  15

Asp Glu Met Asp Val Ser Leu Arg Ala Pro Arg
            20                  25

<210> SEQ ID NO 17
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 17

Arg Ser Ser Ala Ala Gln Leu Thr Ala Ala Arg Leu Lys Ala Leu Gly
 1               5                  10                  15

Asp Glu Leu His Gln Arg Thr Met Trp Arg Arg
            20                  25

<210> SEQ ID NO 18
<211> LENGTH: 27
<212> TYPE: PRT
<213> ORGANISM: Artificial Sequence
<220> FEATURE:

```
<223> OTHER INFORMATION: Description of Artificial Sequence: Peptide
      segment from BH3 domain of a Bcl-2 superfamily
      polypeptide

<400> SEQUENCE: 18

Arg Trp Ala Ala Ala Gln Val Thr Ala Leu Arg Leu Gln Ala Leu Gly
 1               5                  10                  15

Asp Glu Leu His Arg Arg Ala Met Arg Arg Arg
            20                  25

<210> SEQ ID NO 19
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 19

Asp Met Arg Pro Glu Ile Trp Ile Ala Gln Glu Leu Arg Arg Ile Gly
 1               5                  10                  15

Asp Glu Phe Asn Ala Tyr Tyr Ala Arg Arg Val
            20                  25

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 20

Leu Gln Met Leu Lys Gly Glu Lys Leu Gln Val Leu Lys Gly Thr Gly
 1               5                  10                  15

Asp Trp Trp Leu Ala Arg Ser Leu Val Thr Gly
            20                  25

<210> SEQ ID NO 21
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 21

Pro Gly Gly Arg Leu Ala Glu Val Cys Thr Val Leu Leu Arg Leu Gly
 1               5                  10                  15

Asp Glu Leu Glu Gln Ile Arg Pro Ser Val Tyr
            20                  25

<210> SEQ ID NO 22
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 22

Asp Ile Glu Arg Arg Lys Glu Val Glu Ser Ile Leu Lys Lys Asn Ser
```

-continued

```
                  1               5              10              15
Asp Trp Ile Trp Asp Trp Ser Ser Arg Pro Glu
                 20              25
```

<210> SEQ ID NO 23
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 23

```
Ile Ser Ser Ile Gly Tyr Glu Ile Gly Ser Lys Leu Ala Ala Met Cys
 1               5              10              15
Asp Asp Phe Asp Ala Gln Met Met Ser Tyr Ser
                20              25
```

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 24

```
Glu Gly Pro Ala Ala Asp Pro Leu His Gln Ala Met Arg Ala Ala Gly
 1               5              10              15
Asp Glu Phe Glu Thr Arg Phe Arg Arg Thr Phe
                20              25
```

<210> SEQ ID NO 25
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 25

```
Ser Gly Ala Thr Ser Arg Lys Ala Leu Glu Thr Leu Arg Arg Val Gly
 1               5              10              15
Asp Gly Val Gln Arg Asn His Glu Thr Val Phe
                20              25
```

<210> SEQ ID NO 26
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 26

```
Ala Ala Leu Pro Pro Ser Ala Thr Ala Ala Glu Leu Arg Arg Ala Ala
 1               5              10              15
Ala Glu Leu Glu Arg Arg Glu Arg Pro Phe Phe
                20              25
```

<210> SEQ ID NO 27

```
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 27

Met Phe Asp Val Glu Met His Thr Ser Arg Asp His Ser Ser Gln Ser
 1               5                  10                  15

Glu Glu Glu Val Val Glu Gly Glu Lys Glu Val
            20                  25

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 28

Gln Arg Tyr Gly Arg Glu Leu Arg Arg Met Ser Asp Glu Phe Glu Gly
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 29

Gln Arg Tyr Gly Arg Glu Leu Arg Arg Met Ser Asp Glu Phe Val Asp
 1               5                  10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 30

Gly Gln Val Gly Arg Gln Leu Ala Ile Ile Gly Asp Asp Ile Asn Arg
 1               5                  10                  15

<210> SEQ ID NO 31
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 31

Gly Gln Val Gly Arg Gln Leu Ala Leu Ile Gly Asp Asp Ile Asn Arg
 1               5                  10                  15

<210> SEQ ID NO 32
<211> LENGTH: 16
```

```
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 32

Lys Lys Leu Ser Glu Cys Leu Lys Arg Ile Gly Asp Glu Leu Asp Ser
 1               5                  10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 33

Lys Lys Leu Ser Glu Cys Leu Arg Arg Ile Gly Asp Glu Leu Asp Ser
 1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 34

Lys Lys Leu Ser Glu Cys Leu Lys Arg Ile Arg Asp Glu Leu Asp Ser
 1               5                  10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 35

Pro Gly Val His Leu Ala Leu Arg Gln Ala Gly Asp Glu Phe Ser Arg
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 36

Pro Val Val His Leu Thr Leu Arg Gln Ala Gly Asp Asp Phe Ser Arg
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Peptide
```

```
      segment from BH3 domain of a Bcl-2 superfamily
      polypeptide

<400> SEQUENCE: 37

Pro Cys Val His Leu Thr Leu Arg Arg Ala Gly Asp Asp Phe Ser Arg
  1               5                  10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 38

Pro Val Val His Leu Thr Leu Arg Arg Ala Gly Asp Asp Phe Ser Arg
  1               5                  10                  15

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:Description
      of Artificial Sequence : Peptide segment from BH3
      domain of a Bcl-2 superfamily polypeptide

<400> SEQUENCE: 39

Ser Asp Val Arg Gln Ala Leu Arg Asp Ala Gly Asp Glu Phe Glu Leu
  1               5                  10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence:  Peptide
      segment from BH3 domain of a Bcl-2 superfamily
      polypeptide

<400> SEQUENCE: 40

Ala Ala Val Lys Gln Ala Leu Arg Glu Ala Gly Asp Glu Phe Glu Leu
  1               5                  10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence:  Peptide
      segment from BH3 domain of a Bcl-2 superfamily
      polypeptide

<400> SEQUENCE: 41

Arg Asn Ile Ala Arg His Leu Ala Gln Val Gly Asp Ser Met Asp Arg
  1               5                  10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence:  Peptide
      segment from BH3 domain of a Bcl-2 superfamily
      polypeptide

<400> SEQUENCE: 42
```

His Asn Ile Ala Arg His Leu Ala Gln Ile Gly Asp Glu Met Asp His
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 43

Asp Ala Leu Ala Leu Arg Leu Ala Cys Ile Gly Asp Glu Met Asp Val
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence:  Peptide
      segment from BH3 domain of a Bcl-2 superfamily
      polypeptide

<400> SEQUENCE: 44

Gln Leu Thr Ala Ala Arg Leu Lys Ala Leu Gly Asp Glu Leu His Gln
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 45

Gln Val Thr Ala Leu Arg Leu Gln Ala Leu Gly Asp Glu Leu His Arg
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 46

Ile Trp Ile Ala Gln Glu Leu Arg Arg Ile Gly Asp Glu Phe Asn Ala
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 47

Gly Glu Lys Leu Gln Val Leu Lys Gly Thr Gly Asp Trp Trp Leu Ala
1               5                   10                  15

```
<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 48

Ala Glu Val Cys Thr Val Leu Leu Arg Leu Gly Asp Glu Leu Glu Gln
 1               5                  10                  15

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 49

Lys Glu Val Glu Ser Ile Leu Lys Lys Asn Ser Asp Trp Ile Trp Asp
 1               5                  10                  15

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 50

Tyr Glu Ile Gly Ser Lys Leu Ala Ala Met Cys Asp Asp Phe Asp Ala
 1               5                  10                  15

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 51

Asp Pro Leu His Gln Ala Met Arg Ala Ala Gly Asp Glu Phe Glu Thr
 1               5                  10                  15

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 52

Arg Lys Ala Leu Glu Thr Leu Arg Arg Val Gly Asp Gly Val Gln Arg
 1               5                  10                  15

<210> SEQ ID NO 53
<211> LENGTH: 16
<212> TYPE: PRT
```

```
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 53

Ser Ala Thr Ala Ala Glu Leu Arg Arg Ala Ala Ala Glu Leu Glu Arg
 1               5                  10                  15

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 54

Met His Thr Ser Arg Asp His Ser Ser Gln Ser Glu Glu Glu Val Val
 1               5                  10                  15

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence:Peptide
      segment from BH3 domain of a Bcl-2 superfamily polypeptide

<400> SEQUENCE: 55

Lys Asn Leu Trp Ala Ala Gln Arg Tyr Gly Arg Glu Leu Arg Arg Met
 1               5                  10                  15

Ser Asp Glu Phe Glu Gly Ser Phe Lys Gly Leu Lys
            20                  25

<210> SEQ ID NO 56
<211> LENGTH: 27
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 56

Lys Asn Leu Trp Ala Ala Gln Arg Tyr Gly Arg Glu Leu Arg Arg Met
 1               5                  10                  15

Ser Asp Glu Phe Glu Gly Ser Phe Lys Gly Leu
            20                  25

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Peptide
      segment from BH3 domain of a Bcl-2 superfamily
      polypeptide

<400> SEQUENCE: 57

Lys Gly Gln Val Gly Arg Gln Leu Ala Ile Ile Gly Asp Asp Ile Asn
 1               5                  10                  15

Arg
```

```
<210> SEQ ID NO 58
<211> LENGTH: 16
<212> TYPE: PRT
<213> ORGANISM: Artificial Sequence
<220> FEATURE:
<223> OTHER INFORMATION: Description of Artificial Sequence: Leu to Ala
      mutant of SEQ ID NO:30

<400> SEQUENCE: 58

Gly Gln Val Gly Arg Gln Ala Ala Ile Ile Gly Asp Asp Ile Asn Arg
 1               5                  10                  15
```

ENHANCEMENT OF PEPTIDE CELLULAR UPTAKE

CROSS-REFERENCE TO RELATED APPLICATION

The benefit of the filing date of U.S. provisional patent application Ser. No. 60/128,202, filed Apr. 7, 1999, is hereby claimed. The entire disclosure of the aforesaid provisional application is incorporated herein by reference.

FIELD OF THE INVENTION

The invention relates to the field of therapeutics and diagnostics, and in particular to the delivery of biological molecules and other chemical substances into the interior of cells.

BACKGROUND OF THE INVENTION

Many biological molecules and pharmaceutical agents must first traverse the cell membrane in order to exert an action on cells. Transmembrane delivery of nucleic acids, for example, has relied on protein carriers, antibody carriers, liposomal delivery systems, direct injection into cells, electroporation, cell fusion, viral delivery, and calcium-phosphate mediated transformation.

Another method of transmembrane delivery of exogenous molecules, including nucleic acids, has been receptor-mediated endocytosis. This involves conjugating the biological or pharmaceutical agent with a ligand which specifically binds to receptors on a cell membrane. The process of endocytosis is initiated or activated by the binding of the ligand to the receptor. Receptor-mediated endocytosis has been utilized for delivery of proteins as well as nucleic acids to cells. Generally, the ligand is chemically conjugated by covalent, ionic or hydrogen bonding to the exogenous molecule of interest that is still recognized in the conjugate by the target receptor. Conjugation of exogenous molecules of interest to ligand substances having corresponding cell surface receptors is described in U.S. Pat. No. 5,108,921. In particular, the method of the '921 patent relies upon the transmembrane transport of exogenous materials across a membrane having biotin or folate receptors that initiate transmembrane transport of receptor bound species.

International patent application PCT/US90/01002 (WO 90/104448) of Genentech, Inc., discloses covalent conjugates of oligonucleotides and lipids for securing transmembrane delivery of the oligonucleotide into cells. Examples of such lipids include fatty acids and esters thereof, glycerides, e.g., triglycerides, glyceryl ethers, phospholipids, sphingolipids, fatty alcohols, waxes, terpenes, and steroids. The lipids may be naturally derived or synthetically prepared.

International patent application PCT/US90/05272 (WO 91/04753) of Cetus Corporation, describes conjugates of antisense oligonucleotides and ligand-binding molecules which recognize a cell surface receptor. The ligand-binding molecule is a growth factor, an antibody to a growth factor, or an antibody to a cell surface receptor.

U.S. Pat. No. 5,550,111 discloses conjugates of 2', 5'-oligoadenylate and an adduct which results in enhanced penetration into cells. The adduct may comprise a vitamin selected from those vitamins which have a corresponding cell receptor on targeted mammalian cells. Such vitamins include for example, vitamin B12, biotin, riboflavin or folic acid. Alternatively, the adduct may comprise a lipophilic molecule or radical, such as an acyl group of the formula $-OC(CH_2)_xCH_3$, wherein x is an integer from 1 to 20, preferably from 2 to 14.

Frequently, useful effectors of intracellular targets comprise proteinaceous substances such as peptides and polypeptides. For example, the product of the Bcl-2 gene is known to contribute to neoplastic cell expansion by preventing normal cell turnover caused by physiological cell death mechanisms. The Bcl-2 gene product is an intracellular protein. Bcl-2 (B cell lymphomalleukemia 2) was originally identified at the chromosomal breakpoint of t(14;18)-bearing B-cell lymphomas. Bcl-2 is now known to belong to a growing family of proteins which regulate programmed cell death or apoptosis. The Bcl-2 family includes both death antagonists (Bcl-2, Bcl-$x_L$, Bcl-w, Bfl-1, Brag-l, Mcl-l and Al) and death agonists (Bax, Bak, Bcl-$x_S$, Bad, Bid, Bik and Hrk) (Thompson, *Science* 267:1456–62 (1992); Reed, *J. Cell Biol.* 124:1–6 (1994); Yang et al., *Blood* 88:386401 (1996)). This family of molecules shares four homologous regions termed Bcl homology (BH) domains BH1, BH2, BH3, and BH4. All death antagonist members contain the BH4 domain while the agonist members lack BH4. It is known that the BH1 and BH2 domains of the death antagonists such as Bcl-2 are required for these proteins to heterodimerize with death agonists, such as Bax, and to repress cell death. On the other hand, the BH3 domain of death agonists is required for these proteins to heterodimerize with Bcl-2 and to promote apoptosis.

Programmed cell death or apoptosis plays a fundamental role in the development and maintenance of cellular homeostasis. Homologous proteins and pathways in apoptosis are found in a wide range of species, indicating that cellular demise is critical for the life and death cycle of the cell in all organisms. When extracellular stimuli switch on the cell-death signal, the response of the cell to such stimuli is specific for the particular cell type (Bonini et al., *Cell* 72:379–95 (1993)). The pathway to cellular suicide is controlled by certain checkpoints (Oltvai, *Cell* 79:189–92 (1994)). The Bcl family proteins, including both antagonists of apoptosis (such as Bcl-2) and agonists of apoptosis (such as Bax), constitute the primary checkpoint. As such, the transmission of a cell-death signal can be either promoted or blocked by the different combinations of the Bcl-2 family members. The three-dimensional structure of a death antagonist, Bcl-$X_L$, as determined by X-ray crystallography and NMR spectroscopy, provides a structural basis for understanding the biological functions of Bcl-2 family members and for developing novel therapeutics targeting Bcl-2 mediated apoptotic pathways (Muchmore et al., *Nature* 381:335–41 (1996)).

The detailed mechanism of Bcl-2 proteins in mediating molecular pathways of apoptosis has been the subject of intensive investigation. It is known that the apoptotic signaling pathway involves the activation of caspases which, once activated, cleave several cellular substrates such as poly(adenosine diphosphate-ribose) polymerase (PARP) and lead to final events of apoptosis. Bcl-2 plays a crucial role in regulating the process of apoptosis. One possible mechanism for Bcl-2 function is that Bcl-2 inhibits the release of cytochrome c from mitochondria. Cytochrome c is important for the activation of caspases. As such, Bcl-2 blocks caspase activation and subsequent events leading to apoptosis.

Being able to block apoptosis, Bcl-2 is known to contribute to neoplastic cell expansion by preventing normal cell turnover caused by physiological cell death mechanisms. High levels and aberrant patterns of Bcl-2 gene expression are found in a wide variety of human cancers, including ~30–60% of prostate, ~90% of colorectal, ~60% of gastric, ~20% of non-small cell lung cancers, ~30% of neuroblastomas, and variable percentages of melanomas, renal cell, and thyroid cancers, as well as acute and chronic lymphocytic and non-lymphocytic leukemias (Ellis et al., *Cell Biol.* 7, 663 (1991); Henkart, *Immunity* 1, 343 (1994)); Kägi et al., *Science* 265, 528 (1994); Kägi et al., *Nature* 369, 31 (1994); Heusel et al., *Cell* 76, 977 (1994)).

The expression levels of Bcl-2 protein also correlate with relative resistance to a wide spectrum of current chemotherapeutic drugs and ?-irradiation (Hanada et al., *Cancer Res.* 53:4978–86 (1993); Kitada et al., *Antisense Res. Dev.* 4:71–9 (1994); Miyashita et al., *Cancer Res.* 52:5407–11 (1992); Miyashita et al., *Blood* 81:151–7 (1993)). Since Bcl-2 can protect against such a wide variety of drugs which have very different mechanisms of action, it is possible that all these drugs use a common final pathway for the eventual induction of cell death which is regulated by Bcl-2. This notion is supported by the findings that chemotherapeutic drugs induce cell death through a mechanism consistent with apoptosis as opposed to necrosis. Therefore, Bcl-2 can inhibit the cell killing effect of currently available anticancer drugs by blocking the apoptotic pathway.

Because of its role in blocking apoptosis, Bcl-2 plays an important role in many types of cancer. As noted above, Bcl-2 blocks apoptosis, thereby preventing normal cell turnover. As a result, neoplastic cell expansion occurs unimpeded by the normal cellular turnover process. Prostate cancer is one particular example where Bcl-2 has important implication in the pathogenesis and treatment for a disease. Approximately 100,000 new cases of prostate cancer are diagnosed each year in the United States and about 30,000 deaths per year are attributable to this disease (Lynn et al., *JNCl* 87:867 (1995)). It has recently been found that hormone therapy-resistant prostate cancers express Bcl-2 (McDonnell et al., *Cancer Res.* 52:694–04 (1992)), while the normal prostate cells from which prostate cancers originate lack Bcl-2 (Colombel et al., *Am J Pathol* 143:390–400 (1993)). This indicates that Bcl-2 may protect prostate cancer cells from undergoing apoptosis induced by the anticancer drugs, such as taxol (Haldar et al., *Cancer Res.*, 56:1235–5 (1996)). The clinical efficacy of nearly every cytotoxic anticancer drug currently available depends directly or indirectly on the assumption that tumor cells grow more rapidly than normal cells. However, this may not apply to human prostate cancer cells, which show very slow growth kinetics. Tumor kinetics studies have indicated that prostate cancer may be the consequence of the imbalance in cell turnover mechanisms more so than an increase in cell cycle rates. Thus, current anticancer drugs may not be effective in eradicating these nonproliferative prostate cancer cells.

The understanding of the biology of Bcl-2 in cancer and chemoresistance has opened new avenues in the development of novel anticancer strategies. One effective approach to overcome the chemoresistance of prostate cancers is to inhibit the protective function of Bcl-2 proteins. New drugs that modulate Bcl-2 mediated apoptotic response would represent a novel mechanism-based strategy for the treatment of prostate cancers and other cancers. Because the function of Bcl-2 is not absolutely necessary in many normal cell types (Veis et al., *Cell*, 75:229–40 (1993)), a systematic inhibition of Bcl-2 may not affect the normal cellular function. This notion is supported by recent encouraging data from the clinical trial that antisense oligonucleotides targeted against the Bcl-2 gene can specifically inhibit non-Hodgkin's lymphoma in humans (Webb et al., *Lancet* 349:1137–41 (1997)). However, the clinical value of such antisense oligonucleotides is limited by their lack of enzymatic stability, cell permeability, and oral activity. As discussed above, currently available anticancer drugs may not be effective due to the chemoresistance of prostate cancer cells. Therefore, there is an impending need for highly potent, cell permeable, and active Bcl-2 inhibitors as a new generation of effective therapeutics for the treatment of prostate cancer, as well as other cancers.

What is needed is methods and agents for enhancing the cell uptake of drugs and biological molecules used as drugs, particular substances used for regulating apoptosis. In particular, what is needed are methods and agents for enhancing the uptake of peptides and proteins used as inhibitors of intracellular targets, so that these molecules may reach their intended intracellular targets, such as the Bcl-2 protein.

SUMMARY OF THE INVENTION

It is an object of the invention to provide a novel carrier for transporting chemical and biological agents, particularly proteinaceous molecules, across the cell membrane.

It is an object of the invention to provide conjugates of a carrier substance and a chemical or biological agent, particularly a peptide agent, for delivery into the interior of a cell.

It is an object of the invention to provide novel therapeutics and methods for modulating cell apoptosis, particularly for reversing Bcl-2-mediated blockage of cell apoptosis in cancer cells, virally infected cells and self-reactive lymphocytes.

It is an object of the invention to provide agents to overcome Bcl-2-mediated chemoresistance in tumor cells.

These and other objects of the invention are apparent from the following description.

According to the present invention, a peptide conjugate of formula I

is provided wherein:
n is from 1 to 10;
X is
  (a) C=O, when the R—X group is attached to:
    (i) the N-terminus of the peptide, or
    (ii) a side chain of the peptide where the functional group of the side chain to which the R—X group is attached is $NH_2$ or OH; or
  (b) O or NH, when the R—X group is attached to
    (i) the C-terminus of the peptide, or
    (ii) a side chain of the peptide where the functional group of the side chain to which the R—X group is attached is COOH or $CONH_2$; and
R is selected from the group consisting of $C_{2-18}$ alkyl; $C_{2-18}$ alkoxy; $C_{2-14}$ alkylenyl containing one or two double bonds;
cyclobutyl; cyclopentyl; cyclohexyl optionally monosubstituted with a $C_{1-5}$ straight or branched chain alkyl group; phenyl optionally monosubstituted with a $C_{1-5}$ straight or branched chain alkyl group; and benzyl.

In another embodiment of the invention, a method for modulating apoptosis in cells is provided comprising contacting the cells with a conjugate of a molecule which is a modulator of apoptosis and a moiety of the formula II

wherein:

n is from 1 to 10;

X is an atom, chemical bond or chemical group; and

R is as defined above.

When R is alkyl or alkoxy in formulae I or II, the carbon chain may be straight or branched.

Where R is alkyl, it is preferably $C_{3-18}$ alkyl. According to another preferred embodiment, R is $C_{3-6}$ branched chain alkyl. Where R is alkylenyl, it is preferably $C_{2-14}$ alkylenyl containing one double bond or $C_{4-8}$ alkylenyl containing two double bonds.

Where R is $C_{2-14}$ alkylenyl containing two double bonds, the bonds may be conjugated or separated.

Preferred substituted phenyl moieties include 2-phenylethyl, 3-phenylpropyl, 4-phenylbutyl and 5-phenylpentyl.

The peptide moiety of the conjugate of the present invention may consist of natural amino acids, or modified or unnatural amino acids. The peptide is typically comprised of L-amino acids, but may contain one or more D-amino acids.

The peptide may be linear or cyclic. The bonds resulting in cyclization may be between the respective N and C termini of amino acids (main chain to main chain connection), from the N or C terminus of one amino acid to the side chain of another amino acid (main chain to side chain), or from the side chain of one amino acid to the side chain of another amino acid (side chain to side chain connection). The peptide may contain a synthetic backbone modification, such as in the case of a peptidomimetic or peptoid.

When n is 1 in formula I, the R—X group may reside on the peptide C-terminus or N-terminus, or may reside on the side-chain of an amino acid residue. When n is greater than 1 in formula I, the R—X groups can be attached on any positions of the peptide. Preferably, the R—X group is attached to the N-terminus of the peptide, or to the side chain of an amino acid residue.

The invention is also directed to a method for enhancing the cellular uptake of a peptide comprising conjugating said peptide to a carrier moiety $(R-X)_n-$, to form a conjugate as described above.

In one embodiment, the conjugate comprises a peptide which is an inhibitor of the function of an intracellular biological target, such as Bcl-2. According to one such embodiment, the peptide binds to the Bcl-2 protein.

A method is provided for reversing Bcl-2-mediated blockage of apoptosis in cancer cells comprising contacting said cells with a conjugate comprising a peptide which is an inhibitor of the function of Bcl-2.

A method is provided for treating a subject afflicted with a cancer characterized by cancer cells which express Bcl-2. The method comprises administering to the subject an effective amount of a conjugate which comprises a peptide which is an inhibitor of the function of Bcl-2.

In another embodiment of the invention, a conjugate comprises an exogenous molecule, not limited to a peptide, which is a modulator of apoptosis. The modulator is conjugated to a carrier group, $(R-X-)_n-$, as defined above. The modulator may comprise any substance which has the effect of either inducing or inhibiting apoptosis in the target cells. The modulator may comprise a peptide, polypeptide, protein, oligonucleotide, polynucleotide, glycoprotein, oligosaccharide, amino acid, nucleoside, nucleotide, or any other organic molecule which has a modulating effect on apoptosis in cells, particularly cells which are not otherwise permeable to the modulator, absent conjugation to the carrier $(R-X)_n$ as described above.

By "modulator of apoptosis" is meant a substance which either inhibits or induces apoptosis in a cell. By "apoptosis" or "apoptotic death" is meant the programed death which results in controlled autodigestion of the cell, as opposed to necrotic cell death. Apoptotic cell death is characterized by cytoskelet al disruption, cell shrinkage, and membrane blebbing. The nucleus undergoes condensation and nuclear DNA becomes degraded and fragmented. Apoptosis is also characterized by loss of mitochondrial function. Necrotic cell death, on the other hand, is a pathological form of cell death resulting from acute cellular injury, which is typified by rapid swelling and lysis.

According to certain embodiments of the invention, the modulator is an inhibitor of apoptosis, and the target cells induced to undergo apoptosis comprise cancer cells, virus-infected cells or self-reactive lymphocytes. Thus, the conjugates of the invention may be used to treat cancer, viral infection, or autoimmune disorders.

Amino Acid Abbreviations

The nomenclature used to describe polypeptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a three-letter or one letter designation, corresponding to the trivial name of the amino acid, in accordance with the following schedule:

| Alanine | Ala | A |
|---|---|---|
| Cysteine | Cys | C |
| Aspartic Acid | Asp | D |
| Glutamic Acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

Definitions

The following definitions, of terms used throughout the specification, are intended as an aid to understanding the scope and practice of the present invention.

A "peptide" is a compound comprised of amino acid residues covalently linked by peptide bonds. Peptides comprising a large number of amino acids are sometimes called "polypeptides". The expression "peptides" is understood to include "polypeptides" as well as proteins. Further included in the scope of "peptide" as used herein are synthetic variants thereof including various backbone modifications, such as the molecules known as peptidomimetics and peptoids. Further included in the scope of "peptide" as used herein are variants which include alterations of amino acid side chains, including but not limited to attachment of carbohydrate moieties.

The expression "amino acid" as used herein is meant to include both natural and synthetic amino acids, and both D and L amino acids. "Natural amino acid" means any of the twenty primary, naturally occurring amino acids which typically form peptides, polypeptides, and proteins. "Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention.

Amino acids have the following general structure:

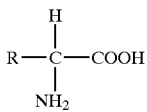

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. The amino acids of the peptides described herein and in the appended claims are understood to be either D or L amino acids with L amino acids being preferred.

DESCRIPTION OF THE FIGURES

FIG. 2 also shows the binding of Bcl-2 protein to two fluorescein-labeled peptides derived from CD4 (E and F) and Bcr-Abl SH3 (H). The lack of binding interaction detected in these control systems (the signals were close to the background level of free Flu-SEQ ID NO:30 (B), demonstrates the specificity of the binding of Flu-SEQ ID NO:30 to Bcl-2.

FIG. 5A: 5 min. incubation with acetyl-SEQ ID NO:55-Biotin; FIG. 5B: 5 min. incubation with decyl-SEQ ID NO:55-Biotin; FIG. 5C: 15 min. incubation with acetyl-SEQ ID NO:55-Biotin; FIG. 5D: 15 min. incubation with decyl-SEQ ID NO:55-Biotin.

DETAILED DESCRIPTION OF THE INVENTION

Figure 1:
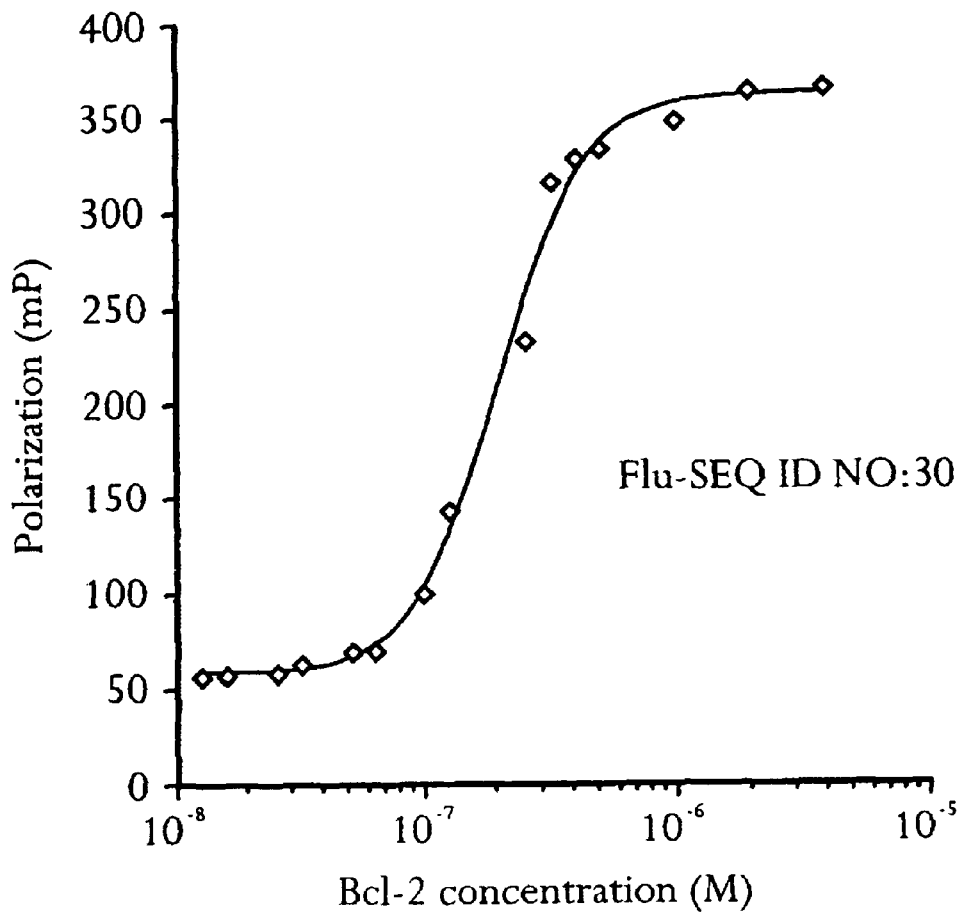
FIG. 1 is a plot of the binding of fluorescein-labeled peptide SEQ ID NO:30 (Flu-SEQ ID NO:30) with Bcl-2 protein. Peptide SEQ ID NO:30 is from the BH3 domain of the human Bak protein.

According to the present invention, the cell penetration of peptides and other exogenous molecules is enhanced by conjugation to a carrier group. The carrier enhances the transmembrane transport of the exogenous molecule. The invention is particularly useful for transporting biologically active molecules which are normally resistant to uptake by normal living cells, such as proteins and polypeptides. The carrier group may be attached to a wide range of molecules, especially a wide range of peptides (inclusive of polypeptides and proteins), by conventional chemistries. Typically, the conjugate is prepared by forming a covalent bond between the carrier group and the exogenous molecule, such as an amide, ester, ether or other organic chemical bond.

According to one preferred embodiment of the invention, the exogenous molecule is a peptide. The peptide is attached to the carrier group through an amino group of a native amino acid in the peptide, or is attached through the side chain of a lysine amino acid added onto the peptide. It may be appreciated that by providing a linking group —NH—, the carrier may be attached through the carboxylic acid side chain of an aspartic acid or glutamic acid residue by formation of an amide bond; by providing an oxygen linking group on the carrier, the carrier may be attached to the peptide through the carboxylic acid side chain of an aspartic acid orglutamic acid residue, forming an ester bond.

According to one embodiment of the invention, the peptide is an exogenous peptide which interacts with an intracellular biological target to evoke a biological response. By "biological target" is meant an enzyme, protein, nucleic acid or other biological molecule with which the exogenous peptide directly or indirectly interacts to bring about a change in the cell. Typically, the peptide is an inhibitor of the function of the biological target. By "intracellular biological target" is meant a biological target which resides substantially inside a cell, as opposed to being resident on the outside of the cell and freely accessible to exogenous chemicals without traversal of the cell membrane. Typically, but not always, the exogenous peptide will exert its effect by binding to the intracellular target inside the cell to evoke the desired biological response in the cell. Alternatively, the exogenous peptide may act by coming in close proximity with the target inside the cell, or otherwise associate with the target. In any event, the action of the exogenous protein on the biological target requires traversal of the former through the cell membrane in sufficient amount to bring about the intended biological response.

Where the peptide exerts its effect by binding to an intracellular biological target molecule, the dissociation constant of the binding is preferably no more than about 100 µM, more preferably no more than about 10 µM, most preferably no more than about 1 µM.

The carrier group of the present invention may be attached to peptides according to well known chemical techniques. According to one preferred method of conjugation, the peptide is synthesized by a solid-phase synthesis technique. Following removal of the FMOC protecting group under normal conditions, the support-bound peptide is treated with an appropriate acid anhydride corresponding to the carrier moiety "R" group (e.g., decanoic anhydride) in dry methylene chloride for 24 hours at room temperature. The reaction solution is removed and the material washed with e.g., methylene chloride and N,N-dimethylformamide and dried in vacuum for 1 hour. The carrier-peptide conjugate is then cleaved from the support with 95% trifluoroacetic acid for 30–60 minutes and then obtained following standard work-up.

One intracellular biological target is the Bcl-2 protein. In this embodiment, the exogenous molecule comprises an inhibitor of Bcl-2 function. Preferably, the inhibitor is a peptide which binds to Bcl-2 and overcomes Bcl-2 antagonism of apoptosis.

A three dimensional structure of Bcl-2 was constructed based on the X-ray and NMR structure of the highly homologous protein BCl-$X_L$ (>98% sequence homology to BCL-2 in the four functionally important BH domains). A hydrophobic binding pocket was found in the structure of Bcl-2 which is formed by the BH1, BH2, and BH3 domains. A highly sensitive Bcl-2 ligand binding assay was then employed to test peptides for specific binding to the hydrophobic surface pocket. This pocket is required for the anti-apoptotic function of Bcl-2; a variety of mutations at his site have been shown to inhibit function of Bcl-2 proteins (Yin et al., Nature 369:321–3, 1994). Peptides which bind the pocket are useful for inhibiting Bcl-2 function.

According to one strategy, peptide inhibitors of Bcl-2 function are designed based upon the amino acid sequence of known endogenous polypeptide inhibitors of Bcl-2. More preferably, the design of the inhibitors is based upon the BH3 domain of the endogenous polypeptide. The BH3 domain of cell death agonist members of the Bcl-2 superfamily of proteins allows these death agonists to heterodimerize with Bcl-2 to promote apoptosis (Zha et al., *J. Biol. Chem.* 271:7440–4, 1996; Chittenden et al., *Embo J.* 14:5589–96, 1995; Boyd et al., *Oncogene* 11:1921–8, 1995).

According to this embodiment of the invention, the amino acid sequence of the peptide inhibitor of Bcl-2 function is identical to the native amino acid sequence of a segment of an endogenous polypeptide inhibitor of Bcl-2, which segment has inhibitory activity to Bcl-2. Alternatively, one or more positions of the corresponding native amino acid sequence of the inhibitory peptide may be substituted with other amino acids. The substitutions preferably comprise conservative amino acid substitutions. A conservative amino acid substitution is a substitution made within a group of amino acids which are categorized based upon the nature of the amino acid side chain. The seven groups are as follows: (1) M, I, L and V; (2) F, Y and W; (3) K, R and H; (4) A and G; (5) S and T; (6) Q and N; (7) E and D. According to one embodiment of the invention, each segment has at least 50%, preferably at least 70%, more preferably at least 80%, most preferably at least 90%, sequence identity with the corresponding native segment of the same length. By "sequence identity" is meant the same amino acids in the same relative positions.

Exemplary peptides for inhibiting the activity of Bcl-2 are listed in Table 1. Smaller peptides are listed in Table 2. Each peptide in Table 1 is a native peptide segment from a Bcl-2 superfamily polypeptide member, homologous to peptide NLWAAQRYGRELRRMSDEFEGSFKGL (SEQ ID NO:1). The latter peptide contains amino acid residues 72–87 from the BH3 domain of the cell death agonist Bad. Each peptide in Table 2 represents a native homolog of the core sequence QRYGRELRRMSDEFEG (SEQ ID NO:28) from peptide SEQ ID NO:1.

TABLE 1

Peptides for Inhibiting Bcl-2 Function

| | |
|---|---|
| NLWAAQRYGRELRRMSDEFEGSFKGL | (SEQ ID NO: 1) |
| NLWAAQRYGRELRRMSDEFVDSFKKGL | (SEQ ID NO: 2) |
| NLWAAQRYGRELRRMSDEFEGSFKGLP | (SEQ ID NO: 3) |
| PSSTMGQVGRQLAIIGDDINRRYDSEF | (SEQ ID NO: 4) |
| PNSILGQVGRQLALIGDDINRRYDTEF | (SEQ ID NO: 5) |
| QDASTKKLSECLKRIGDELDSNMELQR | (SEQ ID NO: 6) |
| QDASTKKLSECLRRIGDELDSNMELQR | (SEQ ID NO: 7) |
| LRPAPPGVHLALRQAGDEFSRRYQRDF | (SEQ ID NO: 8) |
| LSPVPPVVHLTLRQAGDDFSRRYRRDF | (SEQ ID NO: 9) |
| LSPVPPCVHLTLRRAGDDFSRRYRRDF | (SEQ ID NO: 10) |
| LSPVPPVVHLTLRRAGDDFSRRYRRDF | (SEQ ID NO: 11) |
| EIVRASDVRQALRDAGDEFELRYRRAF | (SEQ ID NO: 12) |
| EVIPMAAVKQALREAGDEFELRYRRAF | (SEQ ID NO: 13) |
| QEDIIRNIARHLAQVGDSMDRSIPPGL | (SEQ ID NO: 14) |
| QEEIIHNIARHLAQIGDEMDHNIQPTL | (SEQ ID NO: 15) |
| CMEGSDALALRLACIGDEMDVSLRAPR | (SEQ ID NO: 16) |
| RSSAAQLTAARLKALGDELHQRTMWRR | (SEQ ID NO: 17) |
| RWAAAQVTALRLQALGDELHRRAMRRR | (SEQ ID NO: 18) |
| DMRPEIWIAQELRRIGDEFNAYYARRV | (SEQ ID NO: 19) |
| LQMLKGEKLQVLKGTGDWWLARSLVTG | (SEQ ID NO: 20) |
| PGGRLAEVCTVLLRLGDELEQIRPSVY | (SEQ ID NO: 21) |
| DIERRKEVESILKKNSDWIWDWSSRPE | (SEQ ID NO: 22) |
| ISSIGYEIGSKLAAMCDDFDAQMMSYS | (SEQ ID NO: 23) |
| EGPAADPLHQAMRAAGDEFETRFRRTF | (SEQ ID NO: 24) |
| SGATSRKALETLRRVGDGVQRNHETVF | (SEQ ID NO: 25) |
| AALPPSATAAELRRAAAELERRERPFF | (SEQ ID NO: 26) |
| MFDVEMHTSRDHSSQSEEEVVEGEKEV | (SEQ ID NO: 27) |

TABLE 2

Peptides for Inhibiting Bcl-2 Function

| | |
|---|---|
| QRYGRELRRMSDEFEG | (SEQ ID NO: 28) |
| QRYGRELRRMSDEFVD | (SEQ ID NO: 29) |
| GQVGRQLAIIGDDINR | (SEQ ID NO: 30) |
| GQVGRQLALIGDDINR | (SEQ ID NO: 31) |
| KKLSECLKRIGDELDS | (SEQ ID NO: 32) |
| KKLSECLRRIGDELDS | (SEQ ID NO: 33) |
| KKLSECLKRIRDELDS | (SEQ ID NO: 34) |
| PGVHLALRQAGDEFSR | (SEQ ID NO: 35) |
| PVVHLTLRQAGDDFSR | (SEQ ID NO: 36) |
| PCVHLTLRRAGDDFSR | (SEQ ID NO: 37) |
| PVVHLTLRRAGDDFSR | (SEQ ID NO: 38) |
| SDVRQALRDAGDEFEL | (SEQ ID NO: 39) |
| AAVKQALREAGDEFEL | (SEQ ID NO: 40) |
| RNIARHLAQVGDSMDR | (SEQ ID NO: 41) |
| HNIARHLAQIGDEMDH | (SEQ ID NO: 42) |
| DALALRLACIGDEMDV | (SEQ ID NO: 43) |
| QLTAARLKALGDELHQ | (SEQ ID NO: 44) |
| QVTALRLQALGDELHR | (SEQ ID NO: 45) |
| IWIAQELRRIGDEFNA | (SEQ ID NO: 46) |
| GEKLQVLKGTGDWWLA | (SEQ ID NO: 47) |
| AEVCTVLLRLGDELEQ | (SEQ ID NO: 48) |
| KEVESILKKNSDWIWD | (SEQ ID NO: 49) |
| YEIGSKLAAMCDDFDA | (SEQ ID NO: 50) |

TABLE 2-continued

Peptides for Inhibiting Bcl-2 Function

| | |
|---|---|
| DPLHQAMRAAGDEFET | (SEQ ID NO: 51) |
| RKALETLRRVGDGVQR | (SEQ ID NO: 52) |
| SATAAELRRAAAELER | (SEQ ID NO: 53) |
| MHTSRDHSSQSEEEVV | (SEQ ID NO: 54) |

According to preferred embodiments of the invention, the peptide is selected from the group of peptides of Table 3:

TABLE 3

Peptides for Inhibiting Bcl-2 Function

| | |
|---|---|
| KNLWAAQRYGRELRRMSDEFEGSFKGLK | (SEQ ID NO: 55) |
| KNLWAAQRYGRELRRMSDEFEGSFKGL | (SEQ ID NO: 56) |
| NLWAAQRYGRELRRMSDEFEGSFKGL | (SEQ ID NO: 1) |
| KKLSECLKRIGDELDS | (SEQ ID NO: 32) |
| KKLSECLKRIRDELDS | (SEQ ID NO: 34) |
| GQVGRQLAIIGDDINR | (SEQ ID NO: 30) |
| KGQVGRQLAIIGDDINR | (SEQ ID NO: 57) |

Peptide SEQ ID NOS:1, 30 and 32 comprise the following segments of the BH3 domains of the human Bad, bak and Bax death agonist:

| | |
|---|---|
| SEQ ID NO: 1 | Bad amino acids 72–87; |
| SEQ ID NO: 30 | Bak amino acids 72–87; and |
| SEQ ID NO: 32 | Bax amino acids 52–72. |

It may be appreciated that SEQ ID NOS:55 and 56 represent lysine-extended analogs of SEQ ID NO:1, and that SEQ ID NO:57 represents a lysine-extended analog of SEQ ID NO:30.

Analogs of the aforementioned peptides may be prepared wherein a first amino acid is conservatively substituted with a second, different amino acid. Preferably, the substitution is a conservative substitution. In on embodiment, the analog will share at least about 50%, preferably at least 70%, more preferably at least 80%, most preferably at least 90%, sequence identity with a peptide of Table 1 or 2.

Preferred peptides are characterized by a dissociation constant for Bcl-2 binding of no more than about 100 $\mu$M, more preferably no more than about 10 $\mu$M, most preferably no more than about 1 $\mu$M.

In preferred conjugates of the invention, R is the group $CH_3(CH_2)_nC(O)$— and n is 4, 8, 12 or 16. In preferred peptide conjugates of the invention, R is so selected, and the peptide is selected from Table 3. Particularly preferred are the conjugates designated "octadecyl-SEQ ID NOS:56" and "decyl-SEQ ID NOS:56", which comprise peptide SEQ ID NOS:56 conjugated to $CH_3(CH_2)_{16}C(O)$— and $CH_3(CH_2)_8C(O)$—, respectively. The connection of the R group is through the N-terminus of the peptide in these conjugates:

$CH_3(CH_2)_{16}$COHN-KNLWAAQRYGRELRRMSDEF-EGSFKGL (octadecyl-SEQ ID NO:56)

$CH_3(CH_2)_8$COHN-KNLWAAQRYGRELRRMSDEF-EGSFKGL (decyl-SEQ ID NO:56)

Peptides which bind the Bcl-2 pocket may be identified by a Bcl-2 competition binding assay. The assay is based on fluorescence polarization. The assay can rapidly measure Bcl-2 receptor-ligand interaction without using filter binding, electrophoresis, or precipitation steps. Fluorescence polarization gives a direct, instantaneous equilibrium measure of the bound/free ratio between ligand and receptor molecules.

In order to set up the competition binding assay, the specific binding of a known peptide ligand of the targeted Bcl-2 functional pocket was first demonstrated. The peptide GQVGRQLAIIGDDINR (SEQ ID NO:30) is derived from the BH3 domain of the death agonist Bak. It has been shown in high-resolution X-ray structure to bind strongly to the Bcl-2 pocket (Muchmore et al., Nature 381:33541, 1996; Sattler et al., Science 275:983–6, 1997). Peptide SEQ ID NO:30 was synthesized and labeled with a fluorescein tracer (Flu-SEQ ID NO:30). The binding affinity of Flu-SEQ ID NO:30 to the Bcl-2 protein (purified soluble Bcl-2 proteins purchased from Santa Cruz Biotechnology, Inc., Calif.) was determined by a saturation experiment. Since the polarization value is derived from the ratio of bound versus free tracer, the lowest concentration of Flu-SEQ ID NO:30 was chosen, such that the concentration would yield a reasonable fluorescent signal and a stable polarization value. Using a fixed concentration of Flu-SEQ ID NO:30, Bcl-2 protein was titrated at increasing concentrations to achieve a saturated binding. The binding of the Flu-SEQ ID NO:30 peptide to Bcl-2 protein was measured on a LS-50 luminescence spectrometer equipped with polarizers using a dual path length quartz cell (500 $\mu$L) (Perkin-Elmer Corp.). The fluorophore is excited with vertical polarized light at 485 nm (excitation slit width 10 nm), and the polarization value of the emitted light is observed through vertical and horizontal polarizers at 520 nm (emission slit width 10 nm).

FIG. 1 illustrates a nonlinear least-squares fit for a saturation experiment using Flu-SEQ ID NO:30 and Bcl-2 protein in which the Bcl-2 concentration varied from 6 nM to 2 $\mu$M and the Flu-SEQ ID NO:30 concentration remained at 30 nM. The dissociation constant $K_D$ of Flu-SEQ ID NO:30 was determined to be approximately 0.2 $\mu$M by using a nonlinear least-squares fit and single-site binding mode ($R^2$=0.99).

The binding affinity was also analyzed by Scatchard analysis. The Scatchard analysis is a standard method for analyzing the equilibrium binding parameters of a labeled molecule wily its target protein. The Scatchard plot is sensitive to presence of nonspecific binding, positive or negative cooperativity, and multiple classes of binding sites. The $K_D$ calculated from the Scatchard plot ($K_D$=1/slope), is approximately 0.25 $\mu$M which is in agreement with the value from dose-response calculation ($K_D$~0.20 $\mu$M). The data fit best to linear function, indicating a single class of binding site.

Figure 2:
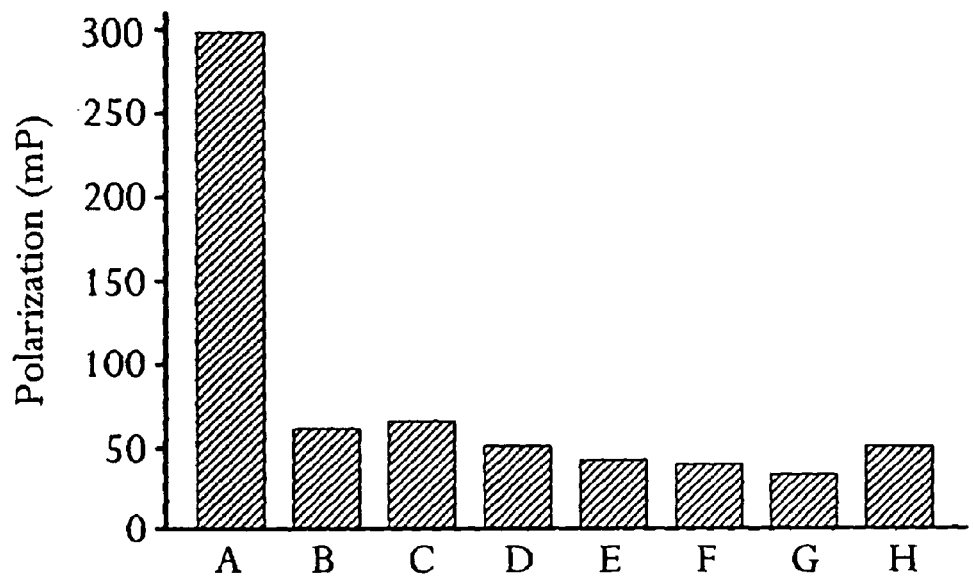
FIG. 2 is a graph of the binding interaction of Flu-SEQ ID NO:30 with Bcl-2 protein (A) and other proteins such as Bax (C), the SH3 domain of the Bcr-Abl oncoprotein (D), and CD4 (E).

To further verify the specificity of the interaction of Flu-SEQ ID NO:30 and Bcl-2, a number of control experiments were carried out including measuring the binding of Flu-SEQ ID NO:30 to other proteins such as Bax, the SH3 domain of the Bcr-Abl oncoprotein, and CD4 (FIG. 2: C, D and E, respectively), and measuring the Bcl-2 binding of other Flu-labeled peptides derived from CD4 (FIG. 2: F and G) and Bcr-Abl SH3 (FIG. 2: H). The lack of binding interaction detected in these control systems (the signals were close to the background level of free Flu-SEQ ID NO:30, FIG. 2: B), demonstrated the specificity of the binding of Flu-SEQ ID NO:30 to Bcl-2 (FIG. 2: A).

Figure 3:
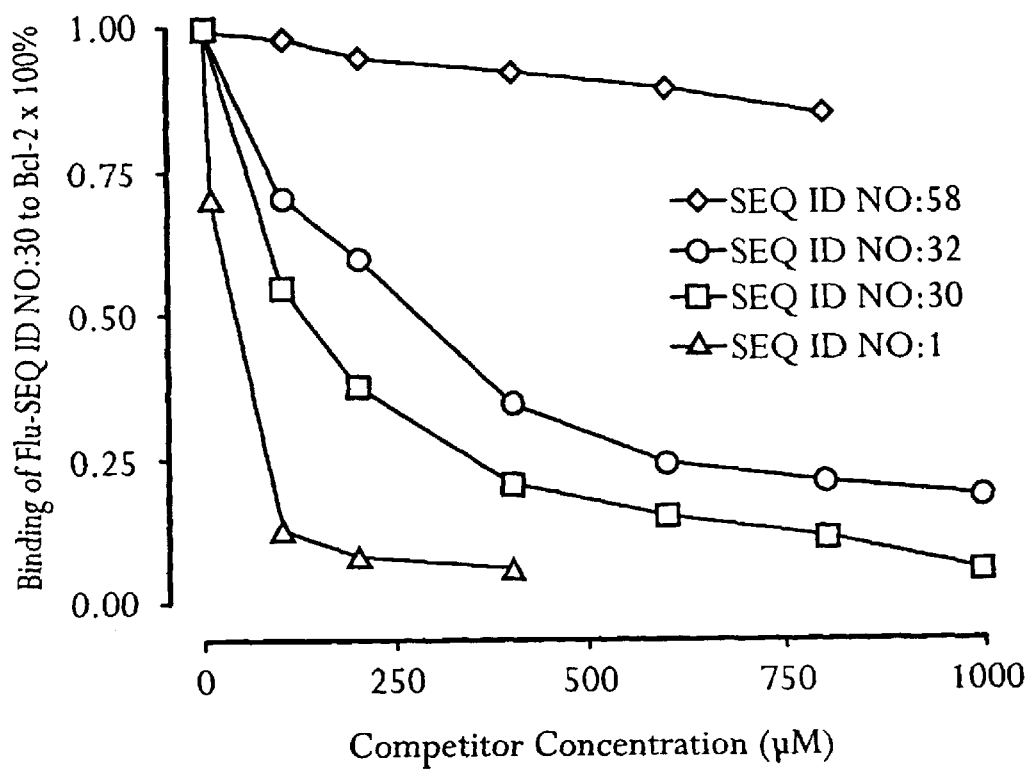
FIG. 3 is a competition curve for the binding of Flu-SEQ ID NO:30 to Bcl-2 protein, in the presence of several peptides derived from BH3 domains of different members of the human Bcl-2 family that bind Bcl-2 or Bcl-XL proteins: SEQ ID NO:1 from BadBH3; SEQ ID NO:32 from BaxBH3; and SEQ ID NO:58, a mutant of BakBH3 peptide SEQ ID NO:30 which contains a leucine-alanine substitution.

To verify this test protocol, competition binding studies were performed with several peptides derived from different human BH3 domains of the Bcl-2 family that have been reported to bind Bcl-2 or Bcl-$X_L$ proteins. These test peptides included the peptide NLWMQRYGRELRRMSDE-FEGSFKGL (SEQ ID NO:1), which was derived from the BH3 domain of the death agonist Bad (BadBH3)and found to be necessary and sufficient to bind the death antagonist BCl-$X_L$ (Kelkar et al., Mol. Cell. Biol. 17:7040–6, 1997); the peptide KKLSECLKRIGDELDS (SEQ ID NO:32) derived from the BH3 domain of the human Bax protein (BaxBH3); and GQVGRQMIIGDDINR (SEQ ID NO:58), a mutant of the BakBH3 peptide SEQ ID NO:30 containing a leucine-alanine substitution. As shown in FIG. 3, a clear dose-dependent inhibition of Bcl-2 binding was observed for the BaxBH3 (SEQ ID NO:32), BakBH3 (SEQ ID NO:30) and BadBH3 (SEQ ID NO:1) peptides. The BadBH3 peptide (SEQ ID NO:1) showed the strongest competition to Flu-SEQ ID NO:30 binding while BaxBH3 (SEQ ID NO:32) and BakBH3 (SEQ ID NO:30) showed weaker activity. The control mutant peptide SEQ ID NO:58 had no significant effect. These results were consistent with those previously reported by other groups employing different binding methods.

Using the fluoresceinated BakBH3 peptide Flu-SEQ ID NO:30 as a specific probe, a competition binding protocol was set up for other peptide and non-peptide organic ligands of Bcl-2. The competition format utilized fixed concentrations of Flu-SEQ ID NO:30 and Bcl-2 proteins (30 nM and 0.55 μM, respectively), with increasing concentrations of inhibitory peptides or organic compounds added to generate inhibition curves. The binding equation proposed by Weinhold et al., *J. Am. Chem. Soc.* 114:9270–9275, 1992, was used to derive the dissociation constant $K_D$ of an inhibitor from petition inhibition curve, $$[\text{Inhibitor}] = \frac{K_D}{K_L}\left[[Bcl-2]x\left(\frac{A_B-A}{A-A_F}\right) - [Flu-SQ30]x\left(\frac{A_B-A}{A_B-A_F}\right)\right] - K_D$$

wherein [Inhibitor], [Bcl-2], and [SQ30] are the concentrations of inhibitor, Bcl-2 protein and Flu-SEQ ID NO:30, respectively; $K_L$ is the dissociation constant of Flu-SEQ ID NO:30; A is the observed fluorescence anisotropy, A=2P/(3-P), where P is the observed fluorescence polarization values; and $A_B$ and $A_F$ are fluorescence anisotropy values when all of the Flu-SEQ ID NO:30 peptide is either bound to the Bcl-2 protein ($A_B$) or free in solution ($A_F$). The $K_D$ value is adjusted by a factor of 5 as suggested by others for fluorescence polarization-based assays.

Figure 4:
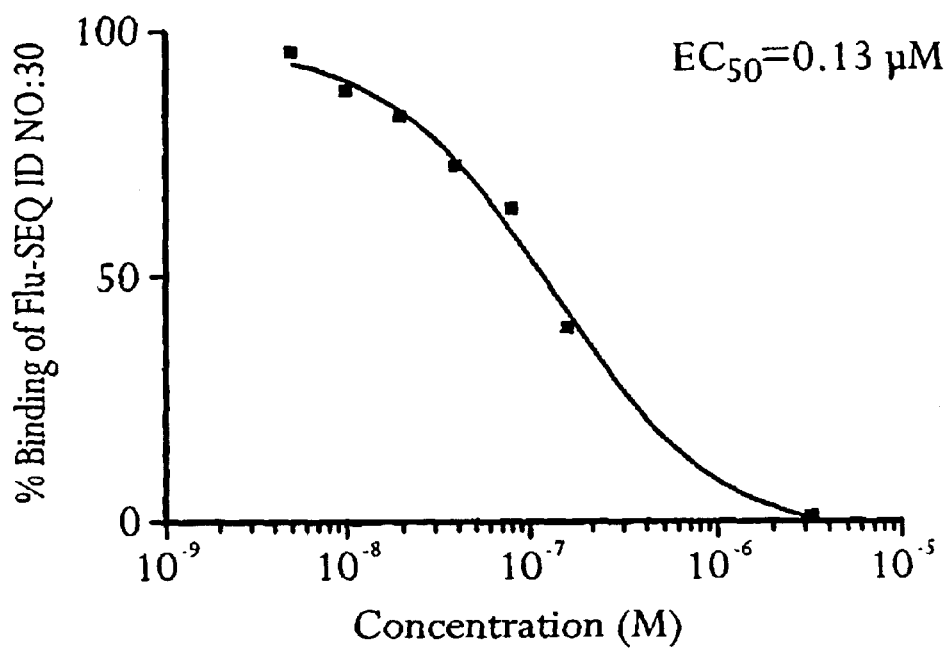
FIG. 4 represents is a competition binding assay between peptide decyl-SEQ ID NO:56 and peptide SEQ ID NO:30 for binding GST-Bcl-2. An EC50 of 0.13 μM for decyl-SEQ ID NO:56 binding to Bcl-2 is determined.

The binding of the Bcl-2 inhibitor conjugate decyl-SEQ ID NO:56 to Bcl-2 was then determined using the competition binding assay with peptide Flu-SEQ ID NO:30. The results are shown in FIG. 4. The $Ec_{50}$ for the Bcl-2 binding of decyl-SEQ ID NO:56 was 0.13 μM, indicating strong binding.

The cell permeability of a conjugate may be verified by directly or indirectly labeling the conjugate with a detectable label which may be visualized inside a cell with the aid of microscopy. For example, a biotinylated derivative of the conjugate may be made by methods well known to those skilled in the art for conjugating biotin molecules to peptides. The biotinylated conjugate is incubated with the relevant target cells in vitro. The cells are harvested and fixed, then stained with Streptavidin-fluorescein and observed in the dark under confocal microscopy. Internalization of the exogenous molecule to which the carrier is conjugated is apparent by fluorescence.

The ability of conjugates of Bcl-2 inhibitors to reverse the cell death antagonism of Bcl-2 and thereby induce cell apoptosis may be determined by the following apoptosis assay. The assay relies on DNA fragmentation as an indicator of apoptosis. Cells of a variant of HL-60 are incubated with carrier-conjugated inhibitor (e.g., carrier-conjugated peptide inhibitor) at 50 μM for two hours. The DNA of the cells is then isolated by conventional techniques and analyzed for fragmentation on 2% agarose gels containing 0.2 μg/ml ethidium bromide.

For peptide conjugates of the present invention, the peptide portion may be a recombinant peptide, a natural peptide, or a synthetic peptide. The peptide may also be chemically synthesized, using, for example, solid phase synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TEA), HCl in dioxane, boron tris-(trifluoroacetate) and cyanogen bromide, and reaction in solution with isolation and purification of intermediates is well-known classical peptide methodology. The preferred peptide synthesis method follows conventional Merrifield solid-phase procedures. See Merrifield, *J. Amer. Chem. Soc.* 85:2149–54 (1963) and *Science* 50:178–85 (1965). Additional information about the solid phase synthesis procedure can be had by reference to the treatise by Steward and Young (*Solid Phase Peptide Synthesis*, W. H. Freeman & Co., San Francisco, 1969, and the review chapter by Merrifield in *Advances in Enzymology* 32:221–296, F. F. Nold, Ed., Interscience Publishers, New York, 1969; and Erickson and Merrifield, *The Proteins* 2:255 et seq. (ea. Neurath and Hill), Academic Press, New York, 1976. The synthesis of peptides by solution methods is described in Neurath et al., eds. (*The Proteins, Vol. II*, 3d Ed., Academic Press, NY (1976)).

Crude peptides may be purified using preparative high performance liquid chromatography. The amino terminus may be blocked according, for example, to the methods described by Yang et al. (*FEBS Lett.* 272:61–64 (1990)).

Peptide synthesis includes both manual and automated techniques employing commercially available peptide synthesizers. The peptides described herein may be prepared by chemical synthesis and biological activity can be tested using the methods disclosed herein.

The peptides described herein may be synthesized in a manner such that one or more of the bonds linking amino acid residues are non-peptide bonds. These non-peptide bonds may be formed by chemical reactions well known to those skilled in the art. In yet another embodiment of the invention, peptides comprising the sequences described above may be synthesized with additional chemical groups present at their amino and/or carboxy termini, such that, for example, the stability, bio-availability, and/or inhibitory activity of the peptides is enhanced. For example, hydrophobic groups such as carbobenzoxyl, dansyl, or t-butyloxycarbonyl groups, may be added to the peptides' amino terminus. Likewise, an acetyl group or a 9-fluorenylmethoxy-carbonyl group may be placed at the peptides' amino terminus. Additionally, the hydrophobic group, t-butyloxycarbonyl, or an amido group, may be added to the peptides' carboxy terminus.

The peptides may be labeled, for further use as biomedical reagents or clinical diagnostic reagents. For example, a peptide of the invention can be conjugated with a fluorescent reagent, such as a fluorescein isothiocyanate (FITC), tetramethylrhodamine isothiocyanate (TRITC), or other fluorescent. The fluorescent reagent may be coupled to the peptide through the peptide N-terminus or free amine side chains by any one of the following chemistries, where R is the fluorescent reagent:

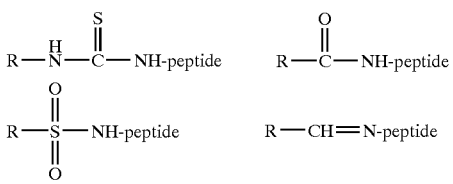

Alternatively, the peptide may be radiolabeled by peptide radiolabeling techniques well-known to those skilled in the art.

In addition to the R—X groups of formulae I and II, the peptides may be engineered to contain additional functional groups to promote cell uptake. For example, carbohydrate moieties such as glucose or xylose may be attached to the peptide, such as by attachment to the hydroxyl function of a serine or threonine amino acid of the peptide. One such conjugate has the structure:

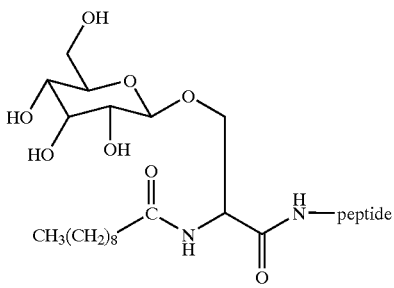

According to one preferred embodiment, the peptide in the conjugate is SEQ ID NO:1.

Further, the peptides of the invention may be synthesized such that their stearic configuration is altered. For example, the D-isomer of one or more of the amino acid residues of the peptide may be used, rather than the usual L-isomer. Still further, at least one of the amino acid residues of the peptide may be substituted by one of the well known non-naturally occurring amino acid residues. Alterations such as these may serve to increase the stability, bioavailability and/or inhibitory action of the peptides of the invention.

Alternatively, the peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Sambrook (*Molecular Cloning*, Cold Spring Harbor Laboratories, Second Ed., 1989), and in Ausubel (*Current Protocols* in *Molecular Biology*, Wiley and Sons, 1987), which are incorporated by reference.

In some embodiments, the peptide conjugates of the present invention may be used in the form of a pharmaceutically acceptable salt.

Suitable acids which are capable of forming salts include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

In one embodiment, the present invention provides methods for treating cancer by inducing apoptosis of cancer cells in an afflicted individual. Accordingly, one or more conjugates of the invention comprising an inducer of apoptosis targeting an intracellular death antagonist (e.g., Bcl-2 protein) is administered to a patient in need of such treatment. A therapeutically effective amount of the drug may be administered as a composition in combination with a pharmaceutical vehicle. In other embodiments of the invention the apoptosis modulator of the carrier conjugate targets a death antagonist associated with virally infected cells or self-reacting lymphocytes to comprise a treatment for viral infection or autoimmune disease.

In particular, conjugates comprising inhibitors of Bcl-2 function may be used to treat any condition characterized by the accumulation of cells which are regulated by Bcl-2. By "regulated by Bcl-2" with respect to the condition of a cell is meant that the balance between cell proliferation and apoptotic cell death is controlled, at least in part, by Bcl-2. For the most part, the cells express or overexpress Bcl-2. Enhancement of Bcl-2 expression has been demonstrated to increase the resistance of cells to almost any apoptotic signal (Hockenbery et al., Nature 348, 334 (1990); Nunez et al., *Immunol.* 144, 3602 (1990); Vaux et al, Nature 335, 440 (1988); Hockenbery et al., *Cell* 75, 241 (1993); Ohmori et al., *Res. Commun.* 192, 30 (1993); Lotem et al., *Cell Growth.Differ* 4, 41 (1993); Miyashita et al., *Blood* 81, 115 (1993); Minn et al.)). Principally, the proliferative disorders associated with the inhibition of cell apoptosis include cancer, autoimmune disorders and viral infections. Overexpression of Bcl-2 specifically prevents cells from initiating apoptosis in response to a number of stimuli (Hockenbery et al., *Nature* 348, 334 (1990); Nunez et al., *J. Immunol.* 144, 3602 (1990); Vaux et al., *Nature* 335, 440 (1988); Hockenbery et al., *Cell* 75, 241 (1993)). The induction of genes that inhibit Bcl-2 can induce apoptosis in a wide variety of tumor types, suggesting that many tumors continually rely on Bcl-2 or related gene products to prevent cell death. Bcl-2 expression has been associated with a poor prognosis in at least prostatic cancer, colon cancer and neuroblastoma (McDonnell et al, Cancer Res. 52, 6940 (1992); Hague et al., *Oncogene* 9, 3367 (1994); Castle et al., *Am. J. Pathol.* 143, 1543 (1993)). Bcl-2 or the related gene Bcl$_x$ has been found to confer resistance to cell death in response to several chemotherapeutic agents (Ohmon et al., *Res. Commun.* 192, 30 (1993); Lotem et al., *Cell Growth- .Differ* 4, 41 (1993); Miyashita et al., *Blood* 81, 115 (1993); Minn et al.)).

Physiologic cell death is important for the removal of potentially autoreactive lymphocytes during development and for the removal of excess cells after the completion of an immune response. Failure to remove these cells can result in autoimmune disease. A lupus-like autoimmune disease has been reported in transgenic mice constitutively overexpressing Bcl-2 in their B cells (Strasser et al., *Proc. Natl. Acad. Sci. USA* 88, 8661 (1991)). Linkage analysis has established an association between the Bcl-2 locus and autoimmune diabetes in non-obese diabetic mice (Garchon et al., *Eur. J. Immunol.* 24, 380 (1994). The conjugates of the invention which comprise inhibitors of Bcl-2 function may be used to induce apoptosis of self-reactive lymphocytes. By "self-reactive" is meant a lymphocyte which participates in an immune response against antigens of host cells or host tissues.

Conjugates comprising inhibitors of Bcl-2 function may be used in the treatment of viral infection, to induce apoptosis of virally infected cells. Viruses have developed mechanisms to circumvent the normal regulation of apoptosis in virus-infected cells, and theses mechanisms have implicated Bcl-2. For example, the E1B 19-kDa protein is instrumental in the establishment of effective adenoviral infection. The apoptosis-blocking ability of E1B can be replaced in adenoviruses by Bcl-2 (Boyd et al., *Cell* 79, 341 (1994)). Genes of certain other viruses have been shown to have sequence and functional homology to Bcl-2 (Neilan et al., *J. Virol.* 67,4391 (1993); Henderson et al., *Proc. Natl. Acad. Sci. U.S.A.* 90, 8479 (1993)). The viral gene LMP-1 specifically upregulates Bcl-2 providing a survival advantage over latently infected cells (Henderson et al., *Cell* 65, 1107 (1991)). Sindbis infection is dependent on the host cell's expression of Bcl-2 (Levine et al., *Nature* 361, 739 (1993)).

In another embodiment, the present invention provides methods for treating disorders characterized by increased apoptosis. In such cases the conjugate of the invention comprises the carrier moiety and an exogenous molecule which is an inhibitor of apoptosis. Such disorders characterized by undesirable apoptosis include, for example, neurodegenerative disorders, AIDS, stroke, and myocardial infarction.

For a review of apoptosis in the pathogenesis of disease, see Thompson, *Science* 267:1456–1462 (1995), the entire disclosure of which is incorporated herein by reference.

Pharmaceutically acceptable vehicles for delivery of the conjugates of the invention include physiologically tolerable or acceptable diluents, excipients, solvents, or adjuvants, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isosteraryl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

Compositions containing the carrier conjugates of the invention may be administered by any convenient route which will result in delivery of the conjugate to cells expressing the intracellular target. Modes of administration include, for example, orally, rectally, parenterally (intravenously, intramuscularly, intraarterially, or subcutaneously), intracistemally, intravaginally, intraperitoneally, locally (powders, ointments or drops), or as a buccalor nasal spray or aerosol.

The pharmaceutical compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small, other preferred routes of administration are intranasal, sublingual, and the like. Intravenous or subcutaneous administration may comprise, for example, injection or infusion.

The conjugates of the present invention may be administered to treat cancer, for example. The effective amount and method of administration will vary based upon the sex, age, weight and disease stage of the patient, whether the administration is therapeutic or prophylactic, and other factors apparent to those skilled in the art. Based upon the in vitro studies described herein, a suitable dosage is a dosage which will attain a tissue concentration of from about 1 to about 100 $\mu$M, more preferably from about 10 to about 75 $\mu$M. It is contemplated that lower or higher concentrations would also be effective. The tissue concentration may be derived from peptide conjugate blood levels.

Such a dosage may comprise, for example, from about 30 to about 80 mg/kg.

According to one preferred embodiment of the invention, the conjugates of the invention which comprise inhibitors of Bcl-2 can be administered as therapeutics to treat any condition which is characterized by the biological function of Bcl-2, as discussed above. In particular, the Bcl-2 inhibitory conjugates may be used to treat cancer, in particular cancers characterized by high levels and/or aberrant patterns of Bcl-2 gene expression. Such increased or aberrant expression is found in a substantial portion of all prostate, colorectal, gastric, non-small lung, renal and thyroid cancers, as well as neuroblastomas, melanomas, and acute and chronic lymphocytic and non-lymphocytic leukemias. In particular the Bcl-2 inhibitory conjugates may be administered in circumstances where the underlying cancer resists treatment with other chemotherapeutics or irradiation, due to the action of Bcl-2 blocking apoptosis. According to one preferred embodiment of the invention, a Bcl-2 inhibitory conjugate is used to treat prostate cancer.

Those skilled in the art will derive appropriate dosages and schedules of administration to suit the specific circumstances and needs of the patient. Doses are contemplated on the order of from about 1 to about 500, preferably from about 10 to about 100, most preferably from about 30 to about 80, mg/kg of body weight. The conjugate may be administered by injection daily, over a course of therapy lasting two to three weeks, for example. Alternatively, the agent may be administered by continuous infusion, such as via an implanted subcutaneous pumps., as is well-known in cancer therapy.

Conjugates according to the present invention may be labeled with a fluorescent, radiographic or other visually detectable label and utilized in vitro studies to identify cells expressing an intracellular target, or to identify the location of the target inside of such cells. For example, a conjugate of the invention may be synthesized with an attached biotin molecule and incubated with cells suspected of expressing the target. The cells are then incubated with streptavidin-fluorescein. Cells expressing the intracellular target will bind the biotin conjugate, and the streptavidin-fluorescein complex. The result is a pattern of fluoresce inside the cell.

In particular, a peptide conjugate of the present invention which binds the Bcl-2 protein may be utilized to identify tumor cells which express Bcl-2 expression. Assessment of Bcl-2 expression has prognostic value, as tumors expressing high to high levels of Bcl-2 are likely to be chemoresistant and/or radiation resistant.

The practice of the invention is illustrated by the following non-limiting examples.

EXAMPLE 1

Fluorescence Polarization Binding Assay of Peptide Conjugate Decyl-SEQ ID NO:56 to Bcl-2

The binding of the peptide conjugate decyl-SEQ ID NO:56 to the Bcl-2 protein was assayed by the following competition assay. Thirty nm of fluorescein-labeled peptide GQVGRQLAIIGDDINR (Flu-SEQ ID NO:30) was incubated with 0.5 µM of GST-Bcl-2 protein. The following micromolar concentrations of decyl-K1285 were then incubated with the mixture for 30 minutes at 37° C. (0.005, 0.01, 0.02, 0.04 0.08 0.16 and 0.32). The values of the binding competition were recorded (FIG. 4) and the EC50 for decyl-SEQ ID NO:56 binding to GST-Bcl-2 was calculated by the PRISMS program as 0.13 µM.

EXAMPLE 2

Cellular Uptake of Peptide Conjugate Decyl-SEQ ID NO:55

The cellular uptake of the peptide conjugate decyl-SEQ ID NO:55 was determined as follows. Peptide SEQ ID NO:55 is identical to peptide SEQ ID NO:56, except for the addition of a C-terminal lysine residue to permit attachment of biotin through the lysine amino side chain.

The SEQ ID NO:55 peptide was synthesized by a solid-phase synthesis technique. Following removal of the FMOC protecting group under normal conditions, the support-bound peptide was treated with decanoic anhydride in dry methylene chloride for 24 hours at room temperature. The reaction solution was removed and the material washed with methylene chloride and NN-dimethylformamide and dried in vacuum for 1 hour. After the removal of the protecting group on the C-terminal lysine, the support-bound decyl peptide was treated with biotin in the presence of 2% hydrazine in N-methylpyrrolidone and 2-(1H-benzotriazole-1-yl)-1,1,3,3-tetramethyluronium hexafluorophosphate. The resulting biotinylated decyl peptide was then cleaved from the support with 95% trifluoroacetic acid for 30–60 minutes. The final product (decyl-SEQ ID NO:55-biotin) was obtained after final work-up as a white solid. In similar fashion, a biotinylated acetyl peptide was prepared (acetyl-SEQ ID NO:55-biotin).

HL-60 cells were incubated with either decyl-SEQ ID NO:55-biotin or acetyl-SEQ ID NO:55-biotin for 5 or 15 minutes at 37° C. The cells were harvested, washed in PBS and fixed in 4% formaldehyde. An aliquot of the fixed cells was smeared on a slide and air dried. The slides was stained with Streptavidin-fluorescein and photographed in the dark under confocal microscopy.

Figure 5A:
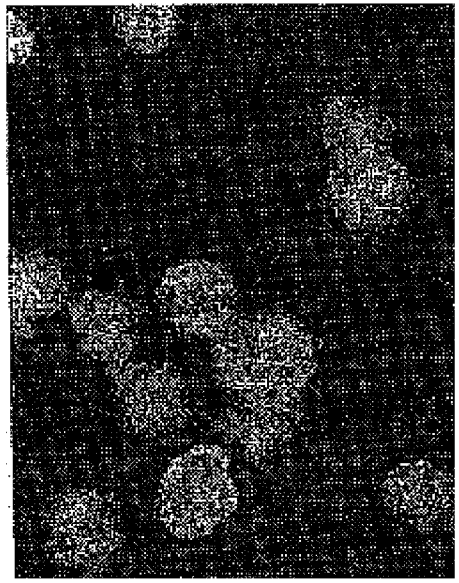
FIGS. 5A through 5D show HL-60 cells which have been treated with biotin-labeled peptide conjugated to an acyl moiety. Acetyl-SEQ ID NO:55 or decyl-SEQ ID NO:55 was biotin labeled and used to treat HL-60 cells for 5 or 15 minutes. The cells were then fixed in formaldehyde and stained with Streptavidin-Fluorescein.
Figure 5B:
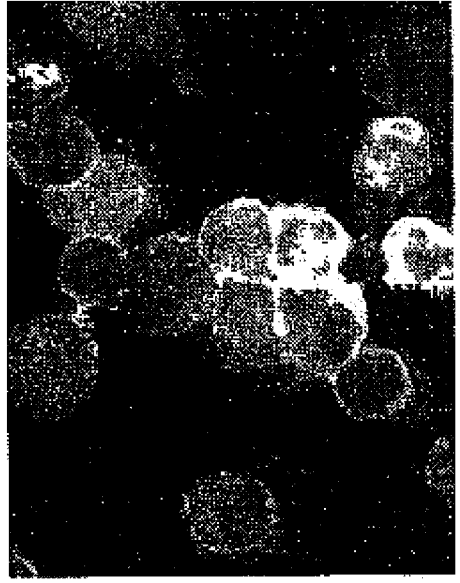
Figure 5C:
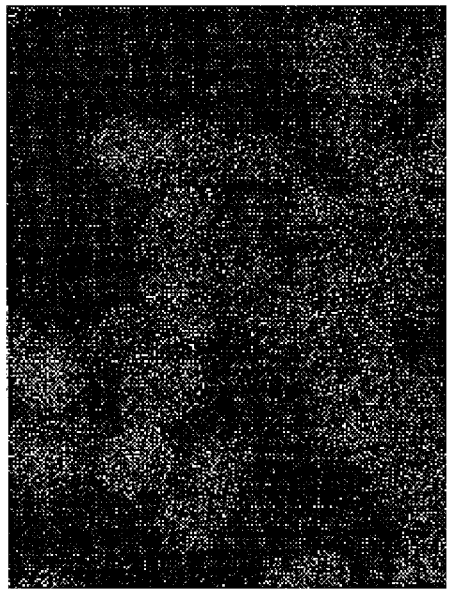

The results are shown in FIGS. 5A–5D. FIG. 5A: acetyl-SEQ ID NO:55-biotin, 5 minutes incubation; FIG. 5B: decyl-SEQ ID NO:55-biotin, 5 minutes incubation; FIG. 5C: acetyl-SEQ ID NO:55-biotin, 15 minutes incubation; and FIG. SD: decyl-SEQ ID NO:55biotin, 15 minutes incubation.

Figure 5D:

Internalization of the peptide in the cells in FIGS. 5B and 5D is apparent by the fluorescence around the cells.

EXAMPLE 3

Apoptosis of HL-60 Cells by Peptide Conjugate Decyl-SEQ ID NO:56

DNA fragmentation is an important and characteristic marker of apoptosis. DNA fragmentation was analyzed in cells treated with the peptide conjugate N-decyl-SEQ ID NO:56. The cells comprised a variant of the human myeloid leukemia HL-60 cell line transfected with Bcl-2 to overexpress Bcl-2 (Liu et al., Cell 86:147–57, 1996). Cells of the parent line are sensitive to 50 µM of the apoptosis-inducing drug etoposide. The Bcl-2-transfected line is resistant to the same concentration of drug, indicating that Bcl-2 blocked apoptosis by the drug.

The Bcl-2-transfected HL-60 cells were incubated for 2 hours with 50 µM of either control (no compound), decanoic acid, unconjugated peptide SEQ ID NO:56, decyl-SEQ ID NO:56, or a decyl-SEQ ID NO:56 mutant in which two amino acid residues of the SEQ ID NO:56 peptide were replaced with alanine. The treated cells were then washed in PBS, lysed in digestion buffer (100 mM NaCl, 10 mM Tris-Cl, pH8, 25 mM EDTA, pH 8, 0.5% SDS, 0.1 mg/ml proteinase K), and incubated overnight at 50° C. The samples were extracted three times with phenol-chloroform, precipitated with an equal volume isopropanol, and spun down for 15 minutes in a microcentrifuge at room temperature. The DNA precipitate was washed once with 70% ethanol and resuspended in TE buffer containing 200 µg/ml DNase-free RNase A (Boehringer Mannheim, Indianapolis, Ind.). Alter incubation at 37° C. for 30 min., the DNA was loaded into a 2% agarose mini-gel with 0.2 µg/ml ethidium bromide, and electrophoresis was run at 50 V for 2 hours in 0.5×TBE buffer. The gel was destained with water for 1 hour arid photographed under UV light. DNA markers were phiX174 DNA with restriction endonuclease Hae III (Boehringer Mannheim).

Figure 6:
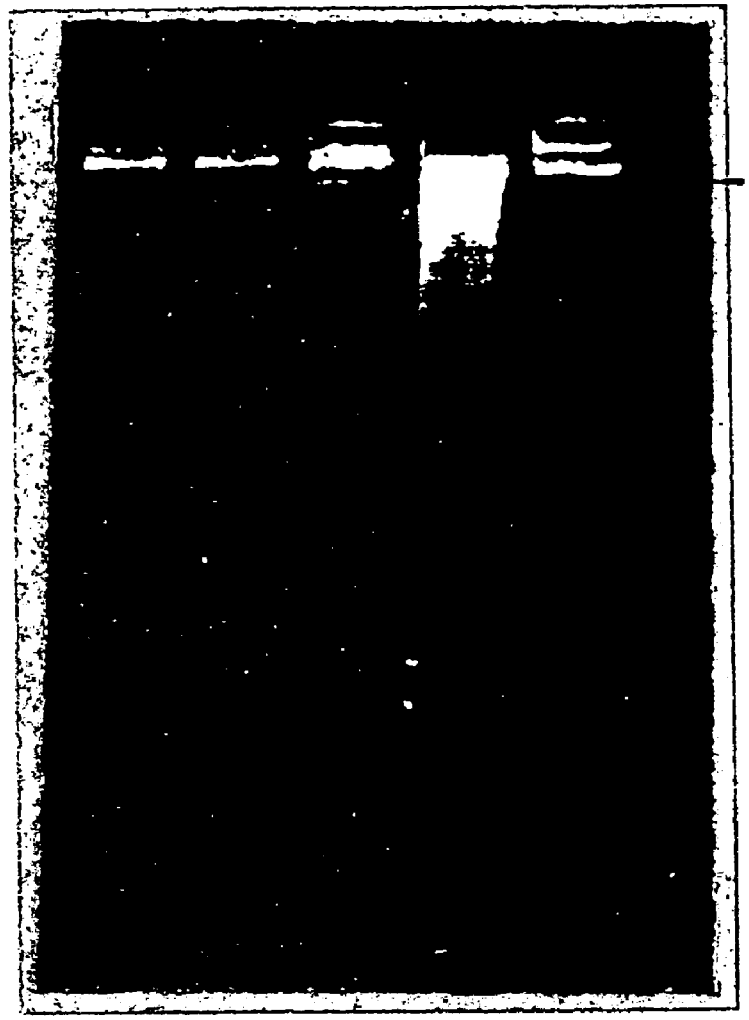
FIG. 6 is a DNA fragmentation assay of HL-60 cells transfected to overexpress Bcl-2 and treated with unconjugated peptide SEQ ID NO:56, carrier (decanoic acid) or carrier-peptide conjugate (decyl-SEQ ID NO:56): lane 0, control; lane 1, decanoic acid; lane 2, unconjugated peptide SEQ ID NO:56; lane 3, decyl-SEQ ID NO:56; and lane 4, a decyl-peptide mutant differing from SEQ ID NO:56 by two amino acids.

The results are shown in FIG. 6: lane 0, control; lane 1, decanoic acid; lane 2, unconjugated peptide SEQ ID NO:56; lane 3, decyl-SEQ ID NO:56; and lane 4, decyl-SEQ ID NO:56 mutant. DNA fragmentation was observed in the decyl-SEQ ID NO:56-treated cells only, again demonstrating the effect of the carrier-peptide conjugates of the invention in penetrating cells and inducing apoptosis of cells regulated by Bcl-2.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A peptide conjugate of the formula I $$(R-X)_n\text{-peptide} \tag{I}$$

wherein:

n is from 1 to 10;

X is
  (a) C=O, when the R—X group is attached to:
    (i) the N-terminus of the peptide, or
    (ii) a side chain of the peptide where the functional group of the side chain to which the R—X group is attached is $NH_2$ or OH; or
  (b) O or NH, when the R—X group is attached to
    (i) the C-terminus of the peptide, or
    (ii) a side chain of the peptide where the functional group of the side chain to which the R—X group is attached is COOH or $CONH_2$;

R is selected from the group consisting of $C_{2-18}$ alkyl; $C_{2-18}$ alkoxy; $C_{2-14}$ alkylenyl containing one or two double bonds; cyclobutyl; cyclopentyl; cyclohexyl optionally monosubstituted with a $C_{1-5}$ straight or branched chain alkyl group; phenyl optionally monosubstituted with a $C_{1-5}$ straight or branched chain alkyl group; and benzyl, and;

the peptide is selected from the group consisting of SEQ ID NOS: 1, 2, 3, 55, 56, and analogs thereof in which one or more amino acids of SEQ ID NOS: 1, 2, 3, 55 or 56 are conservatively substituted with another amino acid.

2. A peptide conjugate according to claim 1 wherein n is 1, 2 or 3.

3. A peptide conjugate according to claim 1 wherein n is 3 to 10.

4. A peptide conjugate according to claim 1 wherein R is $C_{3-18}$ alkyl.

5. A peptide conjugate according to claim 4 wherein R is $C_{3-16}$ branched chain alkyl.

6. A peptide conjugate according to claim 1 wherein R is $C_{2-14}$ alkylenyl containing one double bond.

7. A peptide conjugate according to claim 1 wherein R is $C_{4-8}$ alkylenyl containing two double bonds.

8. A peptide conjugate according to claim 1 wherein the peptide contains at least one D-amino acid.

9. A peptide conjugate according to claim 1 of the formula $CH_3(CH_2)_nC(O)$-peptide wherein n is from 4 to 16.

10. The peptide conjugate of claim 9 selected from the group consisting of $CH_3(CH_2)_{16}$COHN-SEQ ID NO: 56 and $CH_3(CH_2)_8$COHN-SEQ ID NO: 56.

11. A pharmaceutical composition comprising a pharmaceutical vehicle and a peptide conjugate according to claim 1.

* * * * *